United States Patent [19]
Peterson

[11] Patent Number: 5,788,669
[45] Date of Patent: Aug. 4, 1998

[54] PUMP TRACKING SYSTEM

[75] Inventor: Thomas Lloyd Peterson, Shoreview, Minn.

[73] Assignee: SIMS Deltec, Inc., St. Paul, Minn.

[21] Appl. No.: 561,809

[22] Filed: Nov. 22, 1995

[51] Int. Cl.[6] ............................................. A61M 31/00
[52] U.S. Cl. ............................................................ 604/65
[58] Field of Search ............................... 604/65–67, 30, 604/31, 49, 50, 246; 128/DIG. 12, DIG. 13

[56] References Cited

U.S. PATENT DOCUMENTS

| | | | |
|---|---|---|---|
| 3,923,060 | 12/1975 | Ellinwood, Jr. | 128/260 |
| 4,270,532 | 6/1981 | Franetzki et al. | 128/213 R |
| 4,624,661 | 11/1986 | Arimond | 604/151 |
| 4,676,776 | 6/1987 | Howson | 604/31 |
| 4,731,051 | 3/1988 | Fischell | 604/67 |
| 4,754,401 | 6/1988 | Kaczynski et al. | 364/413 |
| 4,756,706 | 7/1988 | Kerns et al. | 604/66 |
| 5,078,683 | 1/1992 | Sancoff et al. | 604/67 |
| 5,153,827 | 10/1992 | Coutre et al. | 364/413.02 |
| 5,256,157 | 10/1993 | Samiotes et al. | 604/246 |
| 5,338,157 | 8/1994 | Blomquist | 417/2 |
| 5,368,562 | 11/1994 | Blomquist | 604/65 |
| 5,594,786 | 1/1997 | Chaco et al. | 379/93 |

FOREIGN PATENT DOCUMENTS 2060151  8/1992  Canada .
0 188 288  7/1986  European Pat. Off. .
665955 A5  6/1988  Switzerland .

Primary Examiner—Michael Buiz
Assistant Examiner—Manuel Mendez
Attorney, Agent, or Firm—Merchant, Gould, Smith, Edell, Welter & Schmidt, P.A.

[57] ABSTRACT

A system for enabling and programming a plurality of pumps wherein each pump can be selectively enabled and loaded with an application program. Each pump also has an interface port. The system comprises a central computer having a storage medium configured to store a plurality of application programs and a remote computer. The remote computer has a first interface arranged and configured to be operatively connected to the interface port of the pumps, a second interface arranged and configured to be operatively connected to the central computer, and circuitry operatively connected to the storage medium, the first interface, and the second interface. The circuitry is configured to generate an enable signal for selectively enabling a pump, and if one of the pumps is operatively connected to the first interface, download an application program from the storage medium in the central computer to the operatively connected pump and transmit the enable signal to the operatively connected pump, thereby causing the pump to become enabled. A data manager stores information to track the application programs and the pumps. A disable signal is generated to later disable the pumps. A security system using checksum values is also provided.

14 Claims, 4 Drawing Sheets 5,788,669

PUMP TRACKING SYSTEM

TECHNICAL FIELD

The present invention relates to a pump tracking system and more particularly to a computer system that can manage and track an inventory of programmable medical pumps.

BACKGROUND

When using a prescribed fluid to treat a patient, it is often beneficial to use an ambulatory pump. The use of an ambulatory pump is helpful because it allows the patient to move around freely. As a result, many patients that are otherwise restricted to the home or a hospital can move more freely. Many such patients can even venture outdoors and remain self-sufficient. This type of delivery is useful in a variety of treatments including chemotherapy, pain control, nutritional supplements therapies, antibiotic treatments, and other types of medical therapies.

Many pumps are software driven so that they infuse fluid into the patient according to a specific therapy. However, a difficulty arises if the pumps are programmed for only one type of therapy. As a result, a hospital must maintain a large inventory of each type of pump in order to handle peak loads. Every time there is a new type of treatment that requires new software, the healthcare provider must purchase new pumps or have existing pumps reconfigured. Maintaining such an inventory is very expensive and needlessly increases the costs of healthcare. Additionally, the software in each pump must be reloaded every time there is an upgrade. Efficient tracking of the software is also a concern in the case of program changes. Efficient tracking of the pumps and pump usage is also a concern.

If each pump is loaded with several different programs so that they can be used for different types of treatment, the user would enable the program that is required for the prescribed therapy. However, if each pump is not loaded with all of the available software, the healthcare provider still needs to maintain a large inventory of different pumps in order to accommodate peak usage. Again, the healthcare provider must purchase new pumps when a new treatment is developed or must reload the software every time there is an upgrade. Also, tracking of the location and use of the software and the pump is a concern.

Therefore, there is a need for a pump tracking system that is flexible and does not require hospitals and clinics to maintain excessively large inventories of pumps.

SUMMARY

The present invention relates to an apparatus for enabling and programming a plurality of programmable medical pumps. Each pump can be selectively enabled and loaded with an application program. Additionally, each pump has an interface port. The apparatus comprises a storage medium configured to store a plurality of application programs and an interface arranged and configured to be operatively connected to the interface port of the pumps. Circuitry is operatively connected to the storage medium and the interface. The circuitry is configured to generate an enable signal for selectively enabling a pump. If one of the pumps is operatively connected to the interface, the circuitry is further configured to download an application program from the storage medium to the operatively connected pump and transmit the enable signal to the operatively connected pump, thereby causing the operatively connected pump to become enabled. A data manager stores information to track the application programs and the pumps. A disable signal is generated when it is desired to disable the pump. A security system using checksum values is preferably provided.

The present invention also provides a system for enabling and programming a plurality of programmable medical pumps. Each pump can be selectively enabled and loaded with an application program. Additionally, each pump has an interface port. The system comprises a central computer having a storage medium configured to store a plurality of application programs and at least one remote computer. The remote computer has a first interface arranged and configured to be operatively connected to the interface port of the pumps, a second interface arranged and configured to be operatively connected to the central computer, and circuitry operatively connected to the storage medium, the first interface, and the second interface. The circuitry is configured to generate an enable signal for selectively enabling a pump, and if one of the pumps is operatively connected to the first interface, download an application program from the storage medium in the central computer to the operatively connected pump and transmit the enable signal to the operatively connected pump, thereby causing the pump to become enabled. A data manager stores information to track the application programs and the pumps. A disable signal is generated when it is desired to disable the pump. A security system using checksum values is preferably provided.

The present invention further includes a method of enabling and programming a pump, wherein the pump has an interface port. The method comprises the steps of operatively connecting the interface port of the pump to the interface of a computer, the computer being configured to generate an enable signal and to store a plurality of application programs. Other steps of the method include downloading one of the plurality of application programs from the computer to the pump, and transmitting an enable signal from the computer to the pump, thereby causing the pump to become enabled. Tracking of the application program and the pump is also provided. Disabling the pump at the desired time is also provided. A security system preferably checks checksum values to avoid non-compatible pumps and programs.

DETAILED DESCRIPTION

Figure 1:
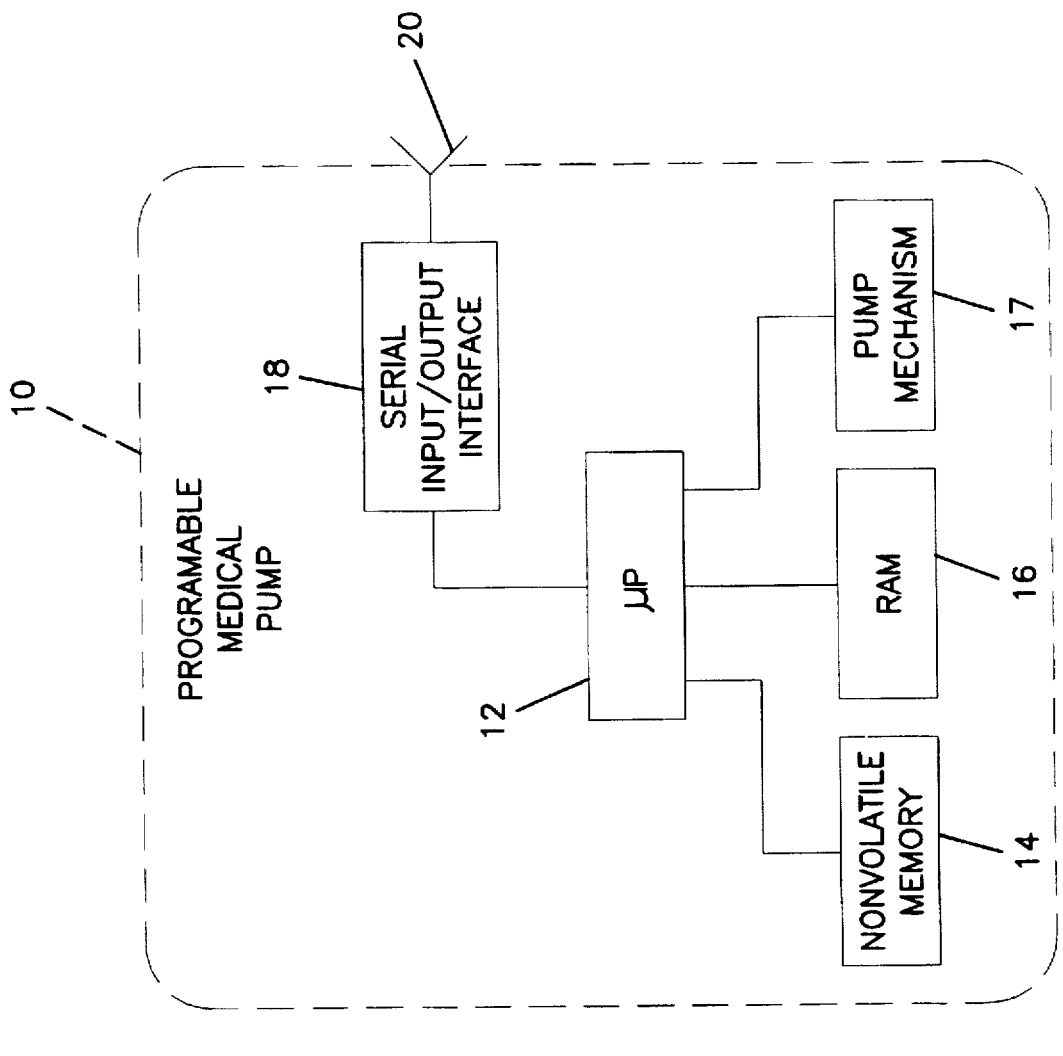
FIG. 1 represents a programmable medical pump that is compatible with the pump tracking system of the present invention.

Following a general description of the pump tracking system of the present invention, an illustrated embodiment of the invention will be described in detail with reference to the drawings, where like reference numerals represent like parts and elements throughout the several views. Reference to the preferred embodiment does not limit the scope of the invention, which is limited only by the scope of the claims attached hereto.

In general terms, the present invention is a pump tracking system that is useful for tracking an inventory of programmable medical pumps that is maintained by a healthcare provider, such as a hospital, clinic, or nursing home. The system includes a computer having memory configured to store a plurality of different application programs. Each application program is designed to control a pump to deliver fluid according to a specific type of therapy. In order to use a pump, it is linked to the computer, which allows a user to select one of the application programs. The user is typically a physician, nurse, or medical technician. The computer downloads the selected program to the linked pump and enables the pump.

The computer can track which application programs are downloaded into a pump and the length of time each pump is enabled. This information is useful for tracking statistics such as the length of time that each pump in the inventory is used and the length of time that each application program is used. Additionally, the computer can include mechanisms to prevent software from being altered or downloaded an unauthorized pump. Such mechanisms enhance safety and prevent piracy.

The present invention has many advantages. One advantage is that the pump tracking system permits the implementation of mechanisms that prevents the use of noncompatible pumps and application programs that have developed a glitch. Such mechanisms provide safety and protection for the patient.

Another advantage is that the pump tracking system can implement mechanisms that prevent the use of pirated application programs and counterfeit pumps. These mechanisms protect the patient by preventing the use of equipment that may have inferior quality. Preventing the use of pirated application programs and counterfeit pumps also reduces the cost of the application programs and pumps. Reducing the price of the equipment is a significant advantage in today's economy where healthcare costs are increasing.

Another advantage is that the present invention enables the pump manufacturer to track the actual time that a particular pump or application program is used. This ability to track the actual use means that the healthcare provider can allocate the cost to the patient that was being treated and does not have build the cost into their general medical fees. As a result, the manufacturer and the healthcare provider can have an arrangement in which fees are paid only for times that the pump and application programs are actually used. Such a fee arrangement could help to keep medical costs under control.

A further advantage is that the present invention can track pump location and application program location on a periodic basis or on demand. Such is useful for generating reports, and keeping close track of inventory.

Referring to FIG. 1, each programmable medical pump 10 has a microprocessor 12, a nonvolatile memory 14, a random access memory 16, and a pump mechanism 17. The pump 10 is encoded with a digitized serial number or unique identification code that can be read through electronic means that are well-known in the art. Pump 10 also includes a serial input/output (i/o) interface 18 that is linked between the microprocessor 12 and an input/output (i/o) port or interface port 20. The nonvolatile memory 14 stores an application program 22 designed to control the pump 10 to deliver fluid according to a specific therapy. The application program 22 is selected from a plurality of different application programs stored in the pump tracking system. U.S. Pat. Nos. 5,338,157 and 5,364,242 describe such a pump in more detail and the disclosures are hereby incorporated by reference.

Figure 2:
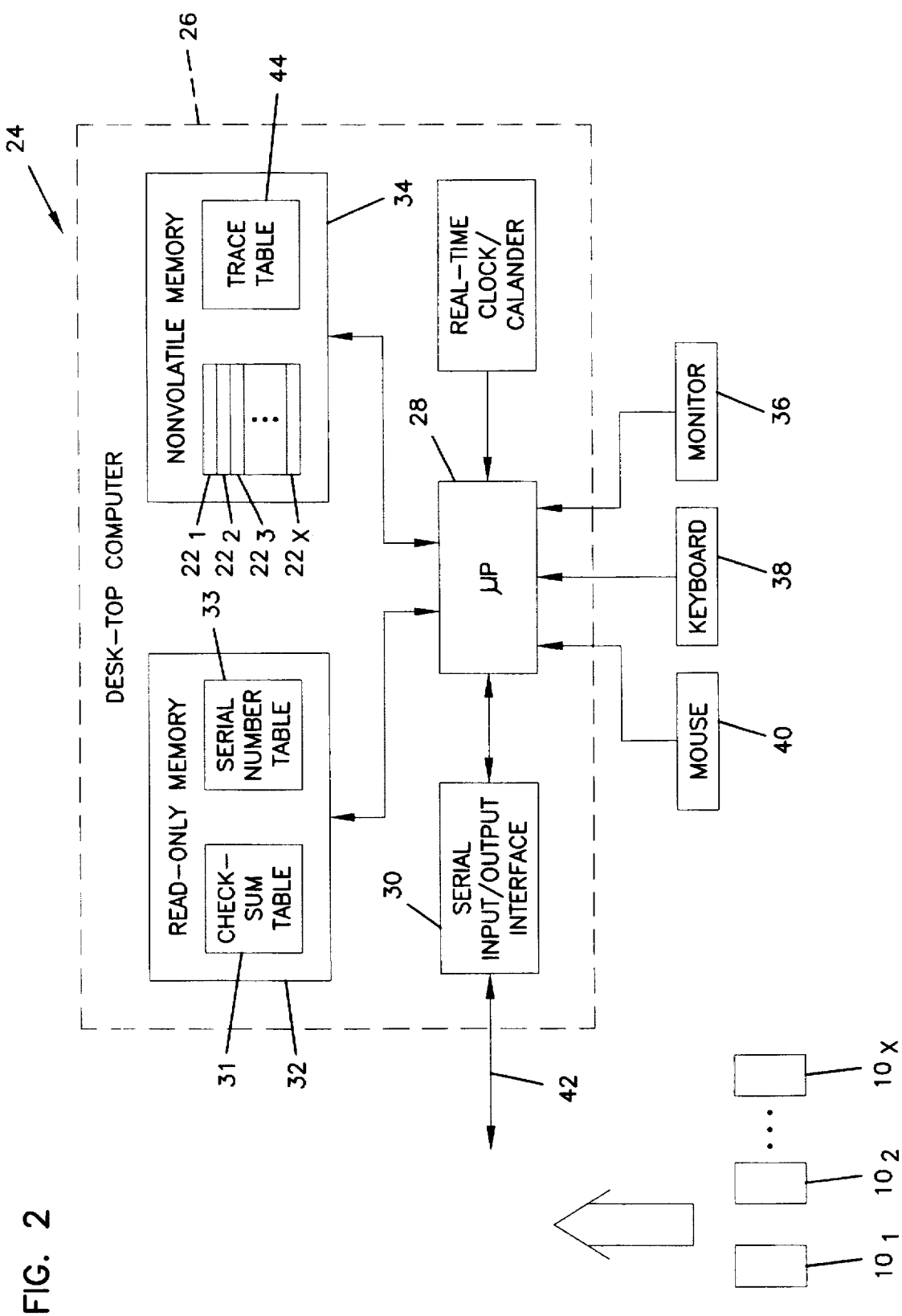
FIG. 2 represents the pump tracking system of the present invention that is compatible with a programmable medical pump as shown in FIG. 1.

Referring to FIG. 2, a pump tracking system, generally shown as 24, includes a desk-top computer 26 that has circuitry such as a microprocessor 28, which is operatively connected to a serial input/output (i/o) interface 30. The microprocessor is operatively connected to a read only memory 32, a non-volatile memory 34, a monitor 36, a keyboard 38 and a mouse 40. The serial i/o interface 30 is operatively connected to an interface cable 42 that is compatible with the i/o port 20 of the pump 10. The serial i/o interface 30 and interface cable 42 form an interface, which enables the pump 10 to be connected to the desk-top computer 26 so that the pump 10 can be either enabled or disable and the selected application program 22 can be downloaded from the desk-top computer 26 to the pump 10.

Downloading can be accomplished by either copying the selected application program 22 to the pump 10 or transferring the selected application program 22 to the pump 10. Copy is advantageous because the selected application program 22 can be downloaded to other pumps.

A healthcare provider that uses the pump tracking system 24 will have a supply of pumps $10_1-10_x$. When a patient needs to receive treatment, a user such as a physician, nurse, or medical technician will take a pump 10 from the supply of pumps $10_1-10_x$. The user will then connect the i/o port 20 of the pump 10 to the interface cable 42 so that the pump 10 is operatively connected to the desk-top computer. The pump 10 then can be loaded with the selected application program 22 and enabled.

The non-volatile memory 34 stores a plurality of application programs $22_1-22_x$ that are available for downloading into the pump 10. In other words, the application program 22 that is downloaded into the pump 10 is selected from the plurality of applications programs $22_1-22_x$ that are stored in the nonvolatile memory 34. Each application program $22_1-22_x$ has a unique identification code that is also stored in the non-volatile memory 34.

The non-volatile memory 34 is also configured to store a trace table 44, which is a database or data manager for tracking use of the pumps $10_1-10_x$ and use of the application programs $22_1-22_x$. Specifically, the trace table 44 can have fields for tracking the serial number of each pump $10_1-10_x$ that is enabled, a first data stamp that indicates the date each pump $10_1-10_x$ is enabled, a second data stamp that indicates the date each pump $10_1-10_x$ is disabled, and an identification code that identifies each application program $22_1-22_x$ that is loaded into one of the pumps $10_1-10_x$. The first and second data stamps can also include information relating to time. The trace table 44 can also include personal and medical information such as the patient's name, address and telephone number, the patient's identification number, the name of the treating physician, the name of the primary nurse, the name of the fluid prescribed, and the delivery protocol. Also, the location of the pump is noted, if different from the patient's address.

The read-only memory 32 is configured to store a checksum table 31 that holds a predetermined checksum value for each application program $22_1-22_x$ stored in the nonvolatile memory 34. The read-only memory 32 is further configured to store a serial number table 33 that includes the serial number of each pump $10_1-10_x$ that is in the hospital's inventory. The read-only memory 32 can be a storage device, such as an EPROM or hardwired circuitry that is configured to contain the required information. However, one skilled in the art will realize that the read-only memory 32 can be any type of storage medium that is difficult for the user to access and tamper with the contents.

The keyboard 38 and monitor 36 are standard devices that are well-known in the computer industry. Additionally, the microprocessor 12 can be operatively connected to a mouse 40 if the system runs on software that uses a graphical user interface such as Windows™ software.

Referring now to FIGS. 1 and 2, the microprocessor 12 of each pump $10_1$–$10_x$ is configured by software that operates and executes as follows. When connected to the desk-top computer 26 via the interface cable 42, the pump 10 taken from the inventory of pumps $10_1$–$10_x$ will generate and transmit a signal that represents the serial number of the pump 10. The serial i/o interface 30 will receive the serial number and then relay the serial number to the microprocessor 28. The microprocessor 28 will compare the serial number of the pump 10 to the serial numbers stored in the read-only memory 32. If the serial number of the pump 10 does not match a serial number stored in the read-only memory 32, the microprocessor 28 will terminate the enablement process and set an error flag.

Terminating the enablement process is a safety feature that prevents use of an unauthorized pump that may not be compatible with the pump tracking system 24 or the programs 22 stored in the non-volatile memory 34. Terminating the enablement process also prevents the use of unauthorized pumps, which protects the pump manufacturer from piracy and the use of counterfeit products if the pumps 10 are leased to the healthcare provider.

If the serial number of the pump 10 does match one of the serial numbers stored in the read-only memory 32, the microprocessor 28 will allow the user to access the application programs $22_1$–$22_x$ stored in the non-volatile memory 34.

The user can then instruct the microprocessor 28 to download an application program 22 selected from the non-volatile memory 34 to the pump 10. When downloading the selected application program 22, the microprocessor 28 will generate a first data stamp, calculate the checksum variable for the selected program 22 and will retrieve the predetermined checksum value that corresponds to the selected program 22. The microprocessor 28 will then compare the calculated checksum value and the predetermined checksum value. If the calculated and predetermined checksum values match, the microprocessor 28 will cause the serial i/o interface 30 to generate and transmit an enable signal that will enable the pump 10. If desired, plural application programs 22 can be downloaded to pump 10.

The microprocessor 28 will also store the following information in the trace table 44: the serial number of the pump 10, the identification number for the selected application program 22 that was downloaded into the pump 10, and the first data stamp. The pump 10 is flagged as being enabled when a first data stamp is stored in the trace table 44 and linked to the pump's serial number, but a second data stamp is not yet stored and linked to the pump's serial number. Additionally, the first data stamp marks the beginning of the time period over which user fees can be accrued.

The user can also enter additional record keeping information such as the name, address, telephone number, and identification number of the patient, the name of the treating physician, the name of the primary nurse, the name of the hospital where the patient is being treated, the prescribed drug, and the delivery protocol. The location of the pump is noted if different from the patient's address. The microprocessor 28 will store the additional information in the trace table 44 and link it to the serial number of pump 10.

If the calculated and predetermined checksum values do not match, the microprocessor 28 will generate an error flag and terminate the enablement process. A failure of the checksum values to match indicates that the selected application program 22 has developed a glitch or has been otherwise altered in some manner. Thus, termination of the enablement process at this point is a safety feature that prevents loading the pump 10 with an application program 22 that does not meet the software developers original specification. Termination of the process at this point also helps prevent use of the pirated software.

When the patient's therapy is complete, a user can reconnect the pump 10 to the interface cable 42 and disable the pump 10. When the pump 10 is connected, it will generate and transmit a signal that corresponds to its serial number. The serial i/o interface 30 will receive the serial number and then relay the serial number to the microprocessor 28. The microprocessor 28 will compare the serial number of the pump 10 with the serial number stored in the read-only memory 32.

If the serial number of the pump 10 does not match one in the read-only memory 32, the microprocessor 28 will set an error flag and will not perform any additional functions with the pump 10. Terminating the disablement process is a safety feature that prevents the pump tracking system 24 from interfacing with a non-compatible pump.

The microprocessor 28 will also compare the serial number of the pump 10 to the serial numbers stored in the trace table 44 and flagged as being enabled. If a match for the serial number of the pump 10 is not found, the microprocessor 28 will set an error flag and will not perform any additional functions with the pump 10. If the serial number of the pump 10 matches one of the serial numbers listed in the read-only memory 32 and one of the serial numbers listed in the trace table 44 and flagged as being enabled, the microprocessor 28 will cause the serial i/o interface 30 to generate and transmit a disable signal to the pump 10.

In response to the disable signal, the pump 10 will write over the program 22 stored in the non-volatile memory 14 and clear the pump's random access memory 16. The microprocessor 28 will also generate a second data stamp and record the second data stamp in the trace table 44. Also, the pump's location can be recorded.

Figure 3:
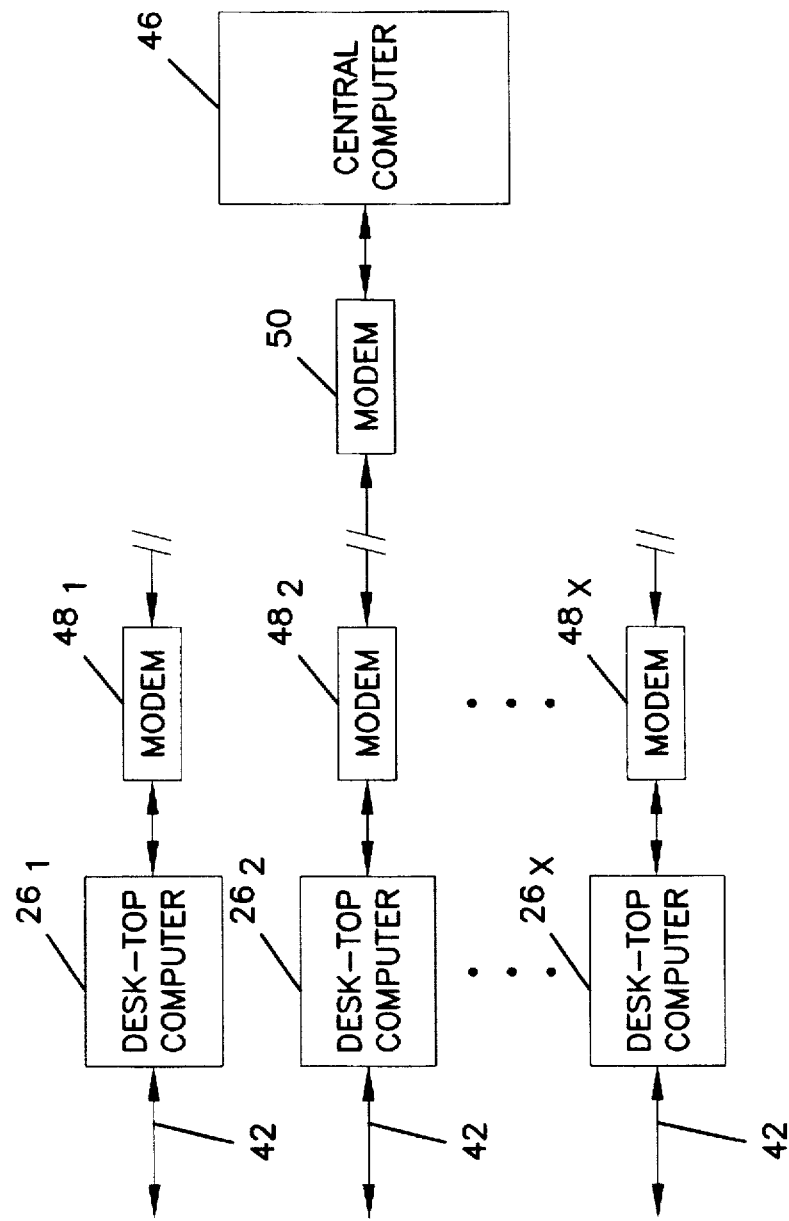
FIG. 3 represents a central computer connected to the pump tracking system shown in FIG. 2.

Referring to FIG. 3, the present invention can include a plurality of desk-top computers $26_1$–$26_x$, each located at a different healthcare provider. Each of the desk-top computers $26_1$–$26_x$ are substantially similar to the desk-top computer 26 shown in FIG. 2 and include the trace table 44 and the interface cable 42. A central computer 46 can access the desk-top computers $26_1$–$26_x$ and then retrieve information stored in each desk-top computer's trace table 44.

In this embodiment, each desk-top computer $26_1$–$26_x$ is operatively connected to a first modem $48_1$–$48_x$, respectively. The central computer is operatively connected to a second modem 50. The central computer 46 can be configured to call each desk-top computer $26_1$–$26_x$ once a month at a predetermined time and upload information from the trace table 44. Once information in the trace table 44 is retrieved, the central computer 46 can instruct the microprocessor 28 to clear all information in the trace table 44 that relates the pumps that have been disabled. Clearing the trace table 44 in this manner will prevent the nonvolatile memory 44 from running out of space. Also, if desired, the trace table 44 can be accessed at any time to upload information needed at that time, such as preliminary use data before the end of the reporting period, or location data in case of a recall or program upgrade. For example, application programs can be traced, so can the pumps themselves.

Using the central computer 46 in this manner is advantageous because a plurality of different healthcare providers can each have a desk-top computer $26_1$–$26_x$ and a supply of programmable medical pumps 10. The pump manufacturer can then access the desk-top computers $26_1$–$26_x$ and download information from the trace tables 44. The manufacturer and/or healthcare providers can use this information for marketing purposes. The manufacturer can also determine the amount of time that each pump 10 is enabled and the amount of time that each application program $22_1$–$22_x$ is downloaded into a pump 10. This information is useful for estimating future user fees or calculating past user fees, which leads to another advantage in that the healthcare provider needs to pay only for the time that the pump 10 is being used to treat a patient. Thus, healthcare costs can be reduced which is an important consideration. Locations of the pumps 10 and the pump application programs 22 can be determined by accessing the trace tables 44. This is useful if the pumps or the pump applications have to be recalled, checked, verified or updated.

Figure 4:
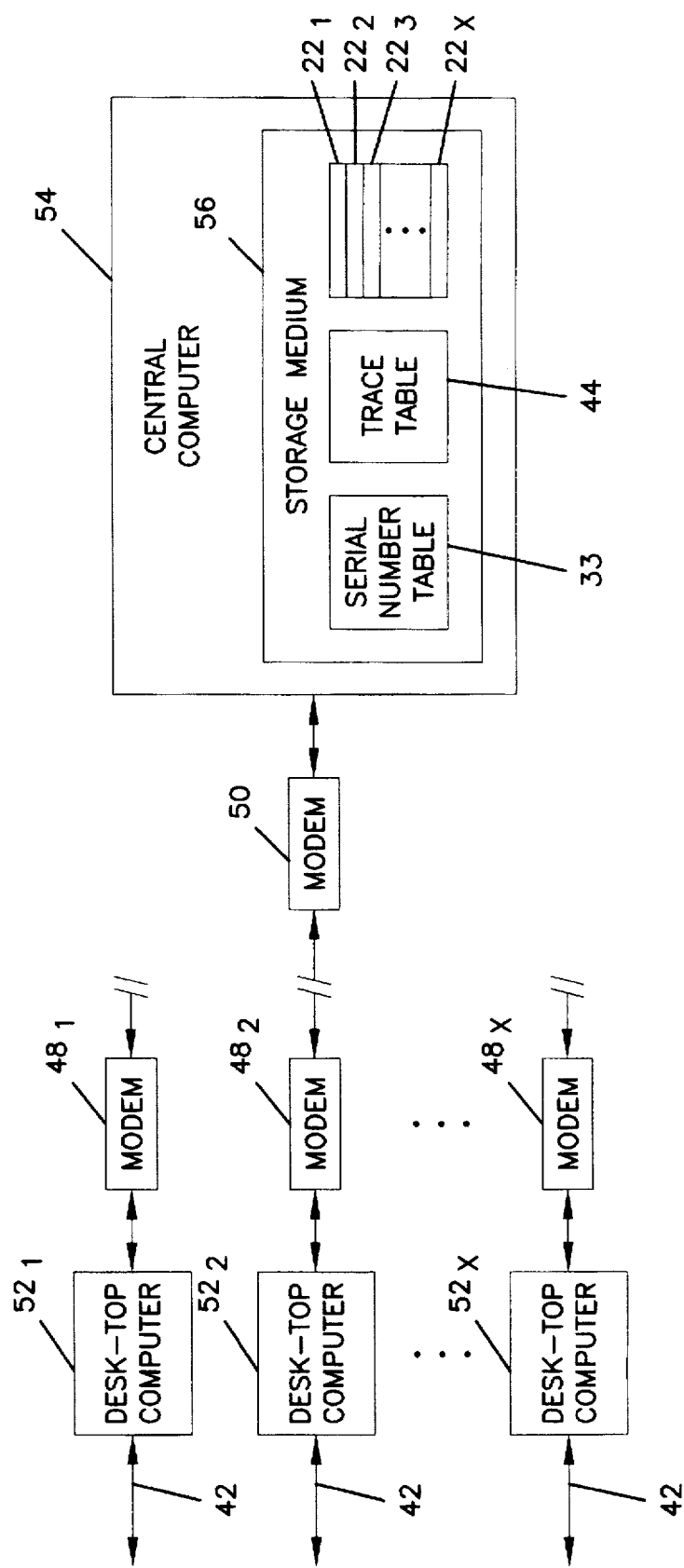
FIG. 4 represents an alternative embodiment of the pump tracking system shown in FIG. 2 and also includes a central computer.

An alternative embodiment of the present invention is shown in FIG. 4. This alternative embodiment includes a plurality of desk top computers $52_1$–$52_x$ and a central computer 54. As in the system shown in FIG. 3, desk-top computers $52_1$–$52_x$ and the central computer 54 can communicate via first modems $48_1$–$48_x$ and second modem 50, respectively.

The central computer 54 is substantially similar to central computer 46, but includes a storage medium 56 that stores the trace table 44, the application programs $22_1$–$22_x$, and the serial number table 33. The desk-top computers $52_1$–$52_x$ are substantially similar to desk-top computer 46 shown in FIG. 2, but does not need to be configured to store the checksum table 32, the serial number table 33, the application programs $22_1$–$22_x$ and the trace table 44.

When a user selects a pump from the supply of pumps $10_1$–$10_x$ and wants to prepare the pump 10 for use, they will connect the pump 10 to the interface cable 42 of the desk-top computer located at the healthcare provider's facility. For purposes of example say the user connects the pump 10 to desk-top computer $52_1$. The pump 10 will generate an identification signal that represents its serial number.

The user causes the desk-top computer $52_1$ to dial up the central computer 54. The desk-top computer $52_1$ will then generate and transmit first and second signals. The first signal embodies a code identifying the healthcare provider and the second signal relays the serial number of the pump 10. The central computer 54 receives the first and second signals and then compares the serial number of the pump 10 and the healthcare provider's identification code to the information stored in the serial number table 33.

If the serial number of the pump 10 matches one of the serial numbers stored in the serial number table 33 and the healthcare providers code matches the code linked to the matched serial number, the central computer 54 will permit the user to select one of the application programs $22_1$–$22_x$ and download the selected program 22 to the pump 10. The selected application program 22 is downloaded via the desk-top computer $52_1$. The central computer 54 will then generate and transmit an enable signal. The desk-top computer $52_1$ receives the enable signal and relays it to the pump 10. Trace table 44 is used in a similar manner to record the enabled pump data.

After therapy is complete, the pump 10 can be disabled in much the same way. The pump 10 is connected to the interface cable 42 of desk-top computer $52_1$ and the central computer 54 verifies the serial number of the pump 10. If the serial number is verified, the central computer 54 will generate and transmit a disable signal to the pump 10 via the desk-top computer $52_1$. Trace table 44 is used in a similar manner to record the disabled pump data.

While the invention has been described in conjunction with specific embodiments thereof, it is evident that different alternatives, alterations, and variations will be apparent to those skilled in the art in view of the foregoing description. Accordingly, the invention is limited only by the following claims, not the described embodiments or the use of elements having specific configurations as presented herein.

The invention that I claim is:

1. An apparatus for enabling and programming a plurality of medical pumps wherein each pump can be selectively enabled and loaded with an application program, further wherein each pump has an interface port and an application program storage memory, each pump requiring receipt of an enable signal and receipt of an application program before each pump is usable to pump fluid to a patient, the apparatus comprising:

a storage medium configured to store a plurality of application programs;

an interface arranged and configured to be operatively connected to the interface port of the pumps; and circuitry operatively connected to the storage medium and the interface, the circuitry being configured to:

selectively generate an enable signal for selectively enabling a pump; and if one of the pumps is operatively connected to the interface, selectively download an application program from the storage medium to the operatively connected pump and transmit the enable signal to the operatively connected pump, thereby causing the operatively connected pump to become enabled;

wherein the circuitry is further configured to selectively generate a disable signal, and if one of the pumps is operatively connected to the interface, selectively transmit the disable signal thereby causing the operatively connected pump to become disabled.

2. The apparatus of claim 1 wherein each of the pumps has an identification code and each of the application programs has an identification code, the pump being configured to transmit an identification signal corresponding to its identification code, the apparatus further comprising a data manager operatively connected to the circuitry, the data manager being configured to:

receive the identification signal upon enabling the operatively connected pump;

store the identification code that corresponds to the received identification signal;

store the identification code for the application program that has been downloaded to the operatively connected pump;

store a first data stamp if the operatively connected pump becomes enabled, the first data stamp corresponding to the time that the operatively connected pump has been enabled.

3. The apparatus of claim 2 wherein the circuitry is further configured to store a second data stamp if the operatively connected pump is disabled, the second data stamp corresponding to the time that the operatively connected pump has been disabled.

4. The apparatus of claim 2 further comprising input means operatively connected to the circuitry, the data manager being further configured to store a name and address of a patient that is being treated with the enabled pump, a name of a facility that has enabled the pump, a name of a physician treating the patient, a location of the enabled pump, and a delivery protocol for treating the patient.

5. The apparatus of claim 2 further comprising a modem operatively connected to the circuitry and a central computer configured to be operatively connected to the circuitry via the modem, the central computer being further configured to:

import the identification code for each pump that has been enabled;

import the identification code for each application program that has been downloaded to a pump;

import the first data stamp; and if the pump has been disabled, import second data stamp.

6. The apparatus of claim 1 wherein the storage medium is further configured to store a plurality of predetermined checksum values, each checksum value corresponding to one of the application programs stored in the storage medium, the circuitry being further configured to:

calculate a checksum value for each application program downloaded from the storage medium;

compare the calculated checksum value with the predetermined checksum value that corresponds to the downloaded application program; and set an error flag if the calculated checksum value does not equal the predetermined checksum value.

7. The apparatus of claim 6 wherein the means for storing a plurality of predetermined checksum values comprises a read-only memory.

8. The apparatus of claim 6 wherein the means for storing a plurality of predetermined checksum values comprises an erasable memory.

9. The apparatus of claim 1, further comprising a plurality of medical pumps, each pump including:

an interface port;

a processor and memory linked to the interface port for storage of at least one application program, the processor capable of receiving the enable signal before pumping to the patient is permitted; and a pump mechanism linked to the processor.

10. A system for enabling and programming a plurality of medical pumps wherein each pump can be selectively enabled and loaded with an application program, further wherein each pump has an interface port and an application program storage memory, each pump requiring receipt of an enable signal and receipt of an application program before each pump is usable to pump fluid to a patient, the system comprising:

a central computer having a storage medium configured to store a plurality of application programs; and a remote computer having:

a first interface arranged and configured to be operatively connected to the interface port of the pumps;

a second interface arranged and configured to be operatively connected to the central computer; and circuitry operatively connected to the storage medium, the first interface, and the second interface, the circuitry being configured to selectively generate an enable signal for selectively enabling a pump, and if one of the pumps is operatively connected to the first interface, selectively download an application program from the storage medium in the central computer to the operatively connected pump and transmit the enable signal to the operatively connected pump, thereby causing the pump to become enabled;

wherein the circuitry is further configured to selectively generate a disable signal, and if one of the pumps is operatively connected to the interface, selectively transmit the disable signal thereby causing the operatively connected pump to become disabled.

11. The system of claim 10 wherein each of the pumps has an identification code and each of the application programs has an identification code, the pump being configured to transmit an identification signal corresponding to its identification code, the central computer further comprising a data manager, the data manager being configured to:

receive the identification signal upon enabling a pump is enabled;

store the identification code for the pump that corresponds to the received identification signal;

store the identification code for the application program that has been downloaded to the enabled pump; and store a first data stamp if the operatively connected pump becomes enabled, the first data stamp corresponding to the time that the pump has been enabled.

12. The system of claim 11 wherein the circuitry is further configured to store a second data stamp if the pump becomes disabled, the second data stamp corresponding to the time that the pump has been disabled.

13. The system of claim 11 further comprising input means operatively connected to the circuitry, the data manager being further configured to store a name and address of a patient that is being treated with the enabled pump, a name of a facility that has enabled the pump, a name of a physician treating the patient, a location of the enabled pump, and a delivery protocol for treating the patient.

14. The system of claim 10, further comprising a plurality of medical pumps, each pump including:

an interface port;

a processor and memory linked to the interface port for storage of at least one application program, the processor capable of receiving the enable signal before pumping to the patient is permitted; and a pump mechanism linked to the processor.

* * * * *